United States Patent
Bayram et al.

(10) Patent No.: US 10,054,367 B2
(45) Date of Patent: Aug. 21, 2018

(54) ASSET LIFE OPTIMIZATION AND MONITORING SYSTEM

(71) Applicant: PaneraTech, Inc., Chantilly, VA (US)

(72) Inventors: Yakup Bayram, Falls Church, VA (US); Alexander Ruege, Fairfax, VA (US); Justin Knowles, Baltimore, MD (US)

(73) Assignee: PANERATECH, INC., Chantilly, VA (US)

( * ) Notice: Subject to any disclaimer, the term of this patent is extended or adjusted under 35 U.S.C. 154(b) by 0 days.

(21) Appl. No.: 15/337,851

(22) Filed: Oct. 28, 2016

(65) Prior Publication Data

US 2017/0131033 A1 May 11, 2017

Related U.S. Application Data

(60) Provisional application No. 62/247,869, filed on Oct. 29, 2015.

(51) Int. Cl.
*G01N 22/02* (2006.01)
*F27D 21/00* (2006.01)
*G01B 15/02* (2006.01)

(52) U.S. Cl.
CPC ........ *F27D 21/0021* (2013.01); *G01B 15/025* (2013.01); *G01N 22/02* (2013.01)

(58) Field of Classification Search
CPC ... G01N 29/036; F27B 5/13; F24F 2011/0013
See application file for complete search history.

(56) References Cited

U.S. PATENT DOCUMENTS

| 5,521,697 A * | 5/1996 | Stavinoha ............... G01J 5/041 250/554 |
| 6,198,293 B1 | 3/2001 | Woskov et al. |
| 9,255,794 B2 | 2/2016 | Walton et al. |
| 9,391,360 B1 | 7/2016 | Bayram et al. |

(Continued)

OTHER PUBLICATIONS

International Search Report issued in copending International Patent Application No. PCT/US16/59469 dated Jan. 31, 2017.

*Primary Examiner* — Jermele M Hollington
*Assistant Examiner* — Alvaro Fortich
(74) *Attorney, Agent, or Firm* — Gregory M. Stone; Whiteford, Taylor & Preston, LLP (57) ABSTRACT

Disclosed is a system to evaluate and monitor the status of a material forming part of an asset, such as a refractory furnace. The system is operative to identify flaws and measure the erosion profile and thickness of different materials, including refractory materials of an industrial furnace, using radiofrequency signals. The system is designed to integrate software with a plurality of sensors and additional hardware to collect data during an inspection of the furnace, even in regions of difficult access. Furthermore, the system comprises a software management subsystem configured to implement signal processing techniques to process the data collected and generate reports to visualize the status, estimate the remaining operational life, and determine the level of penetration of molten material into the surrounding layers of the furnace. Moreover, the system's software enables a user to monitor the status of the furnace both locally and remotely.

26 Claims, 5 Drawing Sheets

(56) References Cited

U.S. PATENT DOCUMENTS

| | | | |
|---|---|---|---|
| 2004/0034442 A1* | 2/2004 | Brower | B21B 37/005 |
| | | | 700/100 |
| 2007/0260378 A1 | 11/2007 | Clodfelter | |
| 2009/0068062 A1* | 3/2009 | Jafari | G01N 1/38 |
| | | | 422/64 |
| 2010/0123467 A1 | 5/2010 | Andarawis et al. | |
| 2013/0120738 A1 | 5/2013 | Bonin et al. | |
| 2013/0144554 A1* | 6/2013 | Walton | G01B 15/02 |
| | | | 702/172 |
| 2013/0245965 A1* | 9/2013 | Kane | G01D 7/00 |
| | | | 702/33 |
| 2014/0340279 A1 | 11/2014 | Bayram et al. | |
| 2015/0109618 A1* | 4/2015 | Howell | G01N 21/39 |
| | | | 356/326 |
| 2015/0276577 A1 | 10/2015 | Ruege et al. | |
| 2015/0362439 A1 | 12/2015 | Bayram et al. | |

\* cited by examiner

ASSET LIFE OPTIMIZATION AND MONITORING SYSTEM

CROSS REFERENCE TO RELATED APPLICATION

This application is based upon and claims priority from U.S. Provisional Patent Application Ser. No. 62/247,869 entitled "ASSET LIFE OPTIMIZATION AND MONITORING SYSTEM" filed with the U.S. Patent and Trademark Office on Oct. 29, 2015, by the inventors herein, the specification of which is incorporated herein by reference.

FIELD OF THE INVENTION

The present invention relates to systems for evaluating the status of a material. More particularly, the present invention relates to systems for monitoring and determining the condition of refractory material using radiofrequency signals.

BACKGROUND OF THE INVENTION

A number of evaluation and monitoring systems have been disclosed within various industries for measuring the properties during and after formation of certain materials, using radiofrequency signals. The surface characteristics, internal homogeneity, thickness, and rate of erosion of a material are some of the important attributes that may require monitoring and evaluation.

On a bigger scale, some industries such as the glass, steel, and plastic industries use large furnaces to melt the raw material used for processing. These furnaces may reach a length equivalent to the height of a 20-story building. Thus, they are a key asset for manufacturers in terms of costs and operational functionality. In order to minimize the internal heat loss at high operating temperatures, these furnaces are constructed using refractory material, having very high melting temperatures and good insulation properties, to create a refractory melting chamber. However, the inner walls of the refractory chamber of the furnace will degrade during operation. The effects of this degradation include inner surface erosion, stress cracks, and refractory material diffusion into the molten material.

In particular, the use of microwave signals to measure the thickness of materials such as furnace walls have been addressed in the prior art, as described in U.S. Pat. No. 6,198,293 to Woskov et al. and U.S. Pat. No. 9,255,794 to Walton et al., the specifications of which are incorporated herein by reference in their entireties. However, these efforts have faced certain challenges and limitations. In particular, attempts made to determine furnace wall thickness on hot furnaces have been generally unsuccessful because of the large signal losses involved in evaluating the inner surface of refractory materials, especially at relatively high frequency bands. Likewise, at relatively low frequency bands signals still experience losses and are limited in terms of the bandwidth and resolution required by existing systems.

Moreover, in placing system components close to the surface of the refractory material to be evaluated, spurious signal reflections make it difficult to isolate the reflected signal of interest, thus further complicating the evaluation of the status of either the inner surface or the interior of such materials. A major challenge is that furnace walls become more electrically conductive as temperature increases. Therefore, signals going through a hot furnace wall experience significant losses making the detection of these signals very challenging.

Additional efforts have been made to evaluate the status of a material, using electromagnetic waves, by reducing the losses and level of spurious signals involved in evaluating refractory materials, as described in U.S. Pat. App. No. 20150362439 by Bayram et al. and U.S. Pat. App. No. 20150276577 by Ruege et al., the specifications of which are incorporated herein by reference in their entireties. However, these systems are primarily aimed to mitigate multiple reflection effects of the electromagnetic waves used for suppression of clutter associated with the received signal. In addition, these attempts have focused on standalone systems lacking integration as a single solution, further requiring software for maximizing the extraction of information from the measured data, and facing challenges to access areas of difficult access in an industrial environment. As a result, these systems are not able to monitor and evaluate a large asset, such as an industrial furnace, for optimizing its operational life, without the support of tracking and software tools.

Currently, there is no well-established integrated system of deterministically and effectively measuring the rate of penetration of molten material into the surrounding refractory material to optimize both the operational life and the maintenance plan of the furnace. As a result, manufacturers experience either an unexpected leakage of molten material through the furnace wall or conservatively shut down the furnace for re-build to reduce the likelihood of any potential leakage, based on the manufacturer's experience of the expected lifetime of the furnace. The lifetime of a furnace is affected by a number of factors, including the operational age, the average temperature of operation, the heating and cooling temperature rates, the range of temperatures of operation, the number of cycles of operation, and the type and quality of the refractory material as well as the load and type of the molten material used in the furnace. Each of these factors is subject to uncertainties that make it difficult to create accurate estimates of the expected lifetime of a furnace.

Moreover, the flow of molten material, such as molten glass, at high temperatures erodes and degrades the inner surface of the refractory material and creates a high risk for molten glass leakage through the refractory wall. A major leak of molten glass through the gaps and cracks in the furnace walls may require at least 30 days of production disruption before the furnace can be restored to operating mode because it needs to be cooled down, repaired, and fired up again. Furthermore, a leak of molten glass may cause significant damage to the equipment around the furnace and, most importantly, put at risk the health and life of workers. For these reasons, in most cases furnace overhauls are conducted at a substantially earlier time than needed. This leads to significant costs for manufacturers in terms of their initial investment and the reduced production capacity over the operational life of the furnace.

Another important issue is that the material used to build the refractory chamber of the furnace may have internal flaws not visible by surface inspection. This could translate into a shorter life of the furnace and pose serious risks during furnace operation. Accordingly, on the one hand the refractory material manufacturer would like to have a means to evaluate the material during manufacture to be able to qualify the material for furnace construction following quality standards to deliver material with no flaws. On the other hand, the customer purchasing the refractory material would like to have a means for performing internal inspections of such material before constructing a furnace.

Thus, there remains a need in the art for systems capable of remotely evaluating the status of such refractory materials, through measurements of propagating radiofrequency signals that avoid the problems of prior art systems.

SUMMARY OF THE INVENTION

An improved system to evaluate and monitor the status of a material forming part of an asset, such as a refractory furnace, is disclosed herein. One or more aspects of exemplary embodiments provide advantages while avoiding disadvantages of the prior art. The system is operative to identify flaws and measure the erosion profile and thickness of different materials, including (by way of non-limiting example) refractory materials of an industrial furnace, using radiofrequency signals. The system is designed to integrate software with a plurality of sensors and additional hardware to collect data during an inspection of the furnace, even in regions of difficult access. Furthermore, the system comprises a software management subsystem configured to implement signal processing techniques to process the data collected and generate reports to visualize the status, estimate the remaining operational life, and determine and report the level of penetration of molten material into the surrounding layers of the furnace. Moreover, the system's software enables a user to monitor the status of the furnace both locally and remotely.

The system transmits a radiofrequency signal into a surface of a material to be evaluated by an antenna disposed contiguous to that surface. The radiofrequency signal penetrates the material and reflects from remote discontinuities. Any voids, flaws, the presence of a different material inside of the material to be evaluated, and any interface of the material with air or other materials may represent a remote discontinuity. The reflected radiofrequency signal is received by the same or a separate antenna, is provided to a control unit comprising a computer-based processor, and timed using as reference the transmitted signal or the signal reflected from the discontinuity between the antenna and the material to be evaluated.

The computer-based processor determines the delay in time between the reference signal and other reflected signals, which may include undesired clutter. Where the magnitude of the clutter is below the magnitude of the signals reflected from remote discontinuities of the material, the computer-based processor identifies a peak level of magnitude associated with these discontinuities and determines the distance from such discontinuities to the surface of the material contiguous to the antenna. One or more evaluations over an area of the material provides the residual thickness of the material and the location of flaws inside the material at each evaluation to create an erosion profile of the remote surface of the material.

In addition, the use of one or more antennas having an alternate configuration and the corresponding data processing allows the generation of cross-sectional images of the inside of the material under evaluation. This becomes particularly useful when evaluating a multilayered structure, such as the layers of refractory material surrounding the molten material in an industrial furnace. As a result, the system is capable of creating a tomographic view within the different layers of material to identify the location of remote discontinuities. More importantly, the system allows for the visualization of the presence of extraneous material within the material under evaluation, such that the penetration of molten material into the insulating material can be detected early.

Therefore, by determining the rate of penetration of molten material into the surrounding material, it is possible to estimate the remaining operational life of the furnace, effectively extending the life of the furnace. This allows more effective and accurate scheduling to optimize the costly processes of furnace repairs, decommissioning, or replacement along with a significant reduction of the level of risk of an operational break or leakage of molten material.

Furthermore, the system comprises a software management subsystem configured to enable a user to control one or more computer-based processors for handling the collected data. This data handling includes measuring, storing, monitoring, recording, processing, mapping, visualizing, transferring, analyzing, tracking, and reporting of these data for evaluating the status of the material under evaluation and generating an accurate estimation of the overall health of the furnace. In addition, the software management subsystem is capable of monitoring and controlling the system operations not only locally, but also remotely through a computer network or a cloud computing environment.

By integrating a number of sensors, additional hardware, and a software management subsystem, and thereby significantly increasing the effective evaluation, monitoring, diagnosing, or tracking of one or more conditions related to the operational health of a furnace, as compared to standard techniques, the system is able to identify and determine the location of flaws and optimize the maintenance scheduling of costly and potentially risky assets.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of particular embodiments of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
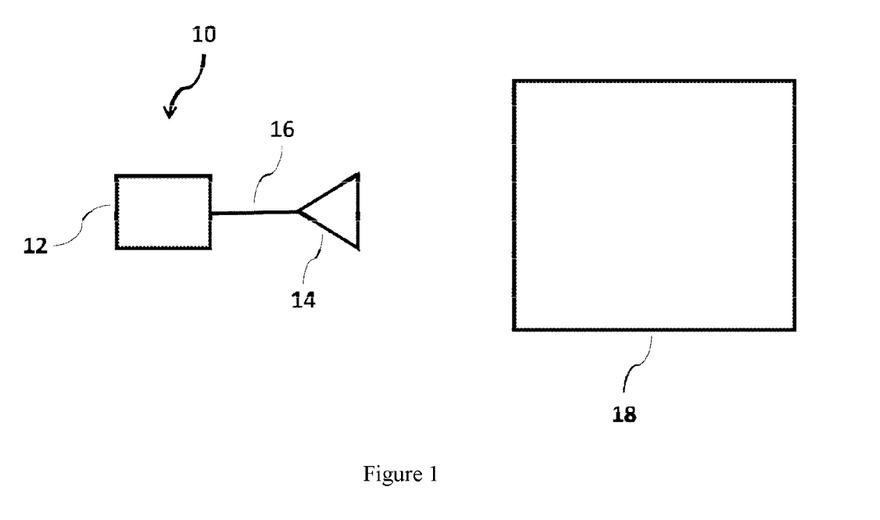
FIG. 1 shows a schematic view of a monitoring system used to evaluate and monitor the status of a unit under test in accordance with certain aspects of a configuration.

In accordance with certain aspects of a configuration of the invention, a schematic top view of the components of a monitoring system 10, used for a typical application of evaluating and monitoring or inspecting a unit under test (UUT) 18, is shown in FIG. 1. Monitoring system 10 comprises a control unit 12, a sensor head 14, and a set of cables 16 to electrically connect or couple control unit 12 and sensor head 14. Sensor head 14 is capable of transmitting one or more electromagnetic (EM) waves into a region around sensor head 14 as well as receiving the corresponding one or more EM waves from that region within a frequency range, preferably in a frequency band of 0.25 GHz to 30 GHz.

Additionally, sensor head 14 may transmit a plurality of EM waves in the frequency domain, such that the time domain representation of this plurality of EM waves corresponds to a radiofrequency (RF) signal of short duration, for example a Gaussian, Rayleigh, Hermitian, or Laplacian pulse or of the like or a combination thereof. Alternatively, sensor head 14 may generate such type of pulse. In any case, the duration of the RF signal is preferably not larger than 5 nanoseconds.

More specifically, sensor head 14 comprises an RF module, and more particularly an RF transceiver, preferably consisting of an RF transmitter and an RF receiver, and one or more antennas or probes. While an exemplary antenna configuration is described herein in accordance with a particularly preferred embodiment, a number of antenna configurations may be suitable for use with the sensor head 14 described herein, and more particularly those antenna configurations set forth in U.S. Pat. No. 9,255,794 of Walton et al., and in U.S. Patent Application Publication No. US 2015/0276577 of Ruege et al., the specifications of which are incorporated herein by reference in their entireties.

Additionally, sensor head 14, apart from frequency domain or time domain RF-based approaches, may also use other technologies such as ultrasound, acoustic, eddy current, gamma rays and similar technologies. Furthermore, sensor head 14 comprises a computer-based processor with an executable computer code or software, capable of measuring and collecting data from the EM waves or RF signals received by sensor head 14, and a data storage unit to store information pertinent to the data collected.

During the inspection process, sensor head 14 is disposed in the vicinity of UUT 18, such that, on the one hand, the signals transmitted by sensor head 14 are launched into the region of UUT 18 to be inspected, whereas on the other hand, the signals transmitted by sensor head 14 that are reflected by UUT 18 may be received by sensor head 14. Furthermore, set of cables 16 comprises one or a combination of more than one of the following: control cables to activate or deactivate sensor head 14, data communication cables for data transfer between control unit 12 and sensor head 14, and power cables to transfer power between control unit 12 and sensor head 14. This allows transmission of both raw data and processed data from sensor head 14 to control unit 12.

In addition, a switch or trigger may be installed along one or more lines of set of cables 16 to enable an in-line trigger that allows partial or total activation or deactivation of the functionality of sensor head 14. Set of cables 16 may also include navigation buttons to assist the operator in tracking the location on UUT 18 to be inspected and communicating with control unit 12.

Control unit 12 comprises a computer-based processor, having executable computer code or software thereon, to control sensor head 14 and to manage the communications and data transfer between control unit 12 and sensor head 14 through set of cables 16. Preferably, control unit 12 further comprises a storage unit to be able to store data and facilitate the processing of the data collected by sensor head 14, and a display unit for displaying information. More preferably, control unit 12 is a portable device. Most preferably, control unit 12 comprises a handheld or wearable electronic device capable of storing and processing data as well as displaying information to a user, including the identification and location of the asset being evaluated, confirmation of the areas already inspected, and the sections pending for inspection. Those skilled in the art will recognize that the transfer of data between control unit 12 and sensor head 14 may be realized through a wireless communication channel via Bluetooth, Wi-Fi, or equivalent methods.

Based on both the known transmitted signals and the signals measured by sensor head 14, a status of UUT 18 may be determined by processing the collected data using the computer-based processor of control unit 12. With continued reference to FIG. 1, it is noted that components of sensor head 14 and the computer-based processors of control unit 12 have not been shown as these components are not critical to the explanation of this configuration.

Figure 2:
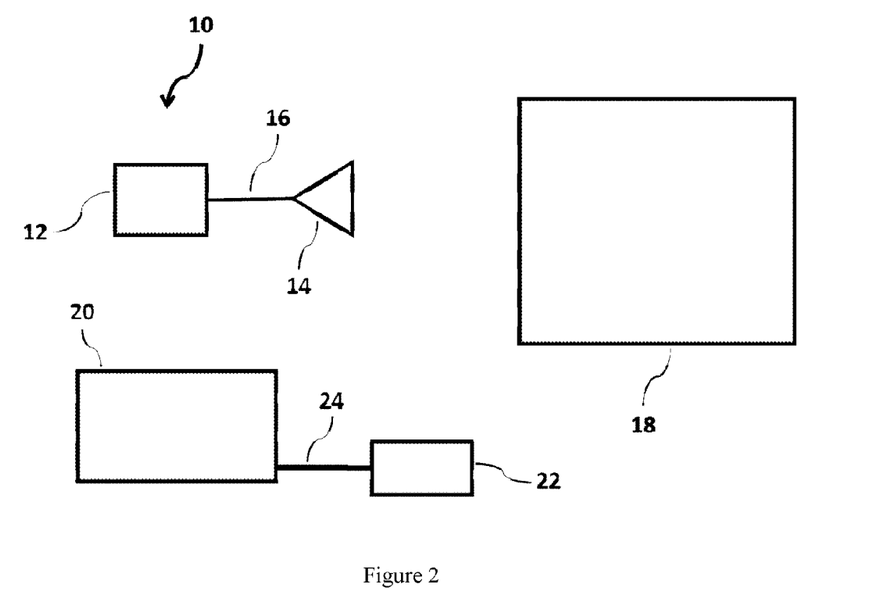
FIG. 2 shows a schematic view of a monitoring system used to evaluate and monitor the status of a unit under test in accordance with certain aspects of another configuration, wherein a computer-based processor is used for data processing.

FIG. 2 shows a schematic top view of monitoring system 10 in accordance with certain aspects of another configuration, wherein a computer-based processor 20, having executable computer code or software thereon, is used to process the data collected by sensor head 14. In addition, the data processed by computer-based processor 20 may be visually shown in a display 22, which is connected to computer-based processor 20 through cable 24. Computer-based processor 20, display 22, and cable 24 are commonly used devices that are well known in the prior art.

Preferably, sensor head 14 transfers the data associated with UUT 18, through set of cables 16, to control unit 12, which communicates with computer-based processor 20. Those skilled in the art will realize that various methods exist to transfer the data collected by sensor head 14 to computer-based processor 20 for further processing and displaying, including a portable memory device that stores such data, a wired cable connecting control unit 12 or sensor head 14 to computer-based processor 20, and a wireless communication channel between control unit 12 or sensor head 14 and computer-based processor 20.

Figure 3:
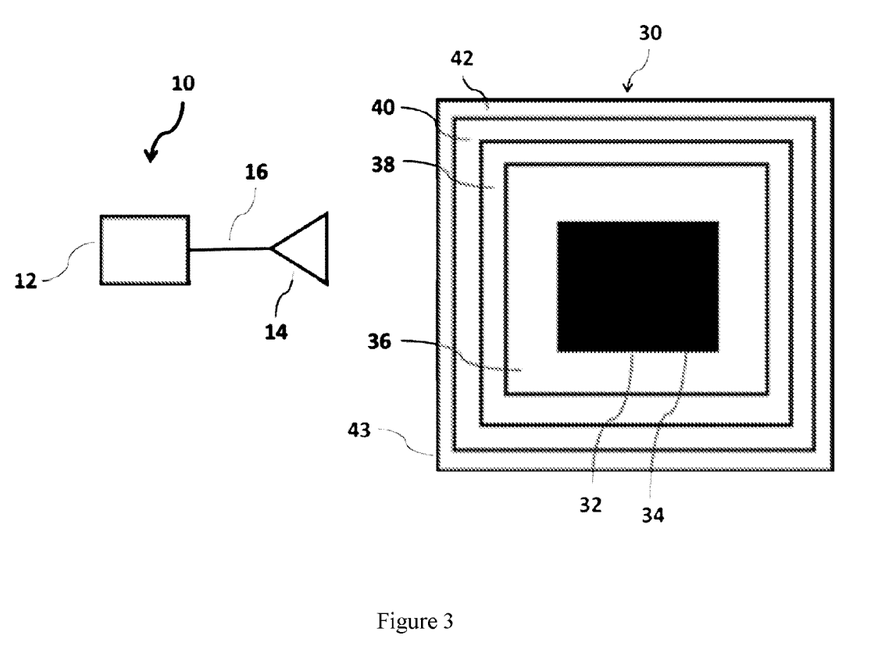
FIG. 3 shows a schematic view of a monitoring system used to evaluate and monitor the status of a furnace using a sensor head.

FIG. 3 shows a particular configuration of monitoring system 10 in which UUT 18 consists of a furnace 30, comprising a chamber 32 enclosing a molten material 34, and a first layer 36, a second layer 38, a third layer 40, and a fourth layer 42, wherein each of these layers is made of refractory or insulating materials. Furnace 30 is representative of applications used in the glass, steel, and plastic industries. In these applications, chamber 32 is typically surrounded by multiple layers of material to prevent heat loss and leakage of molten material to the outside of furnace 30 and as a safety measure to workers and equipment operating in the surroundings of furnace 30.

Each of layers 36, 38, 40, and 42 has an outer surface and an inner surface opposite the outer surface, such that the inner surface is closer to chamber 32. Thus, the inner surface of first layer 36 of refractory material is contiguous to (i.e., in physical contact with) chamber 32. Normally, during operation of furnace 30, the inner walls of chamber 32 will degrade. The effects of this degradation include inner surface erosion, stress cracks, and refractory material diffusion into the molten material. Accordingly, molten material 34, such as molten glass, at high temperatures erodes and degrades the inner walls of chamber 32 and surrounding layers 36, 38, 40, and 42, creating a high risk of molten material leakage to the outside of furnace 30. Typical thickness values of refractory and insulation material of furnace walls range from 1 inch to 24 inches on the sidewalls.

In general, monitoring a certain status of furnace 30 depends on the specific sensor head 14, disposed in the vicinity of outer surface 43 of furnace 30, used to collect data and connect to control unit 12 through set of cables 16. In particular, the use of a refractory thickness sensor as sensor head 14, enables monitoring system 10 to determine the thickness and thickness profile of one or more of layers 36, 38, 40, and 42 of furnace 30. Alternatively, the use of a furnace tomography sensor as sensor head 14, enables monitoring system 10 to determine a thickness profile and assess the degree of penetration of molten material 34 into one or more of layers 36, 38, 40, and 42 of furnace 30. Those skilled in the art will realize that a plurality of sensors of the same type in either a monostatic or multistatic configuration, and other types of sensors may be used as sensor heads, including thermal imaging, temperature, and furnace bottom detection sensors.

Figure 4:
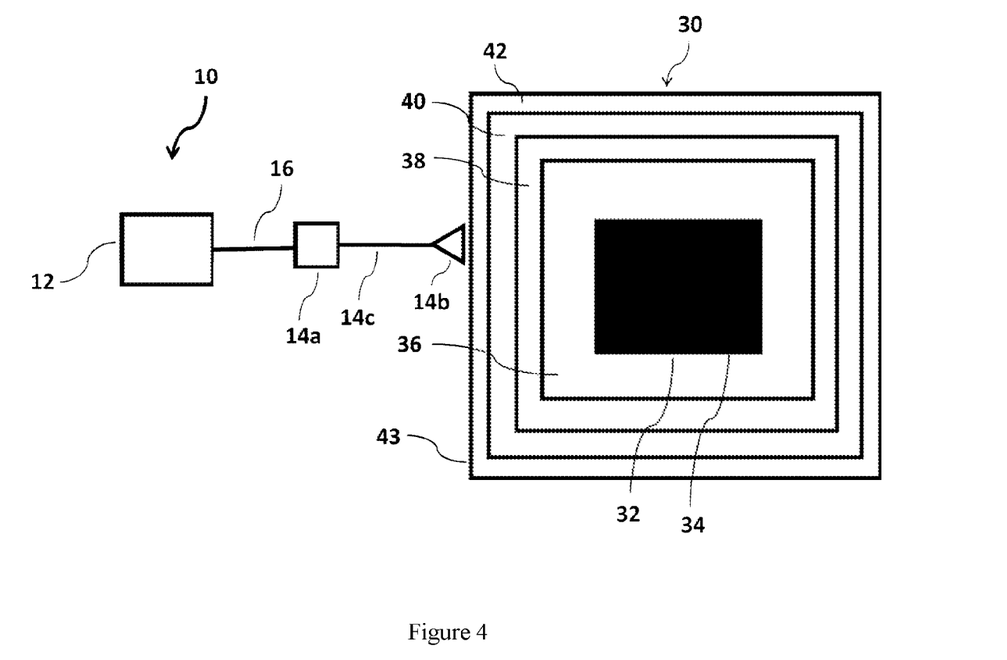
FIG. 4 shows a schematic view of a monitoring system used to evaluate and monitor the status of a furnace using a probe.

Typically, in industrial applications the access to certain regions of furnace 30 might be particularly difficult. FIG. 4 shows an alternative configuration of monitoring system 10, wherein sensor head 14 comprises three components: namely, an electronic device 14a comprising an RF transceiver, a computer-based processor with executable computer code or software thereon, and a data storage unit; an antenna or probe 14b; and a cable 14c, such as a coaxial cable, to electrically connect device 14a to probe 14b. This configuration allows setting up a unit of smaller size in the vicinity of outer surface 43 of furnace 30, because probe 14b is separated from electronic device 14a.

Furthermore, one or more probes 14b may be permanently or temporarily installed in-situ over a plurality of locations of furnace 30, especially in areas of difficult access. Preferably, in-situ probes 14b are installed in the vicinity of outer surface 43 of furnace 30. Then, device 14a may connect to each probe 14b through connectorized cable 14c to collect the data corresponding to the area wherein each probe 14b is installed. Probe 14b need not be in physical contact with furnace 30 and can be mechanically actuated by a switch or trigger button located on control unit 12 or set of cables 16. Similarly, probe 14b can be quickly activated by attaching a quick-connect cable 14c. In addition, a plurality of sensors with communication capabilities may be installed in each of layers 36, 38, 40, and 42 or chamber 32, enclosing molten material 34, to provide data to probe 14b. Preferably, this plurality of sensors is installed during furnace construction or during a repair process.

Moreover, a mechanical attachment, such as a pole, using a quick-connect system to easily connect to probe 14b may be used to prioritize usability of monitoring system 10, to increase the accessibility of probe 14b, and to extend the locations of furnace 30 that may be reachable by probe 14b. Preferably, the mechanical attachment is extendable and flexible, such as a gooseneck type for accessing tight spots, and provides certain self-alignment with a wall of furnace 30. More preferably, the mechanical attachment is also rugged, light weight, and collapsible to fit into a carry-on sized case. Those skilled in the art will realize that other types of mechanical attachments may be used to enhance the access of probe 14b to areas of furnace 30 that may be difficult to access. These mechanical attachments may include telescopic poles, foldable elements, angled-section arms, and retractable parts.

In reference to FIGS. 1 to 4, in a preferred configuration, control unit 12 is capable of controlling and handling a plurality of sensor heads 14 and probes 14b. The computer-based processor and the executable software of control unit 12 may enable the identification of the type of sensor head 14 connected to control unit 12 or the type of probe 14b attached to device 14a, by initiating a handshaking protocol between control unit 12 and sensor head 14 or device 14a. This handshaking protocol is similar to the one used by a computer to recognize a flash drive. Accordingly, once the type of sensor head 14 or probe 14b is identified, control unit 12 operates sensor head 14 or device 14a for monitoring the corresponding status of furnace 30.

Typically, control unit 12 is capable of connecting to a variety of sensor heads 14 and probes 14b. Those skilled in the art will realize that a number of other types of sensors may be connected to control unit 12, including temperature sensors to determine temperature profiles and furnace bottom sensors to determine the distance between the bottom of chamber 32 and outer surface 43 of furnace 30 in the area substantially parallel to the floor wherein furnace 30 is installed.

Figure 5:
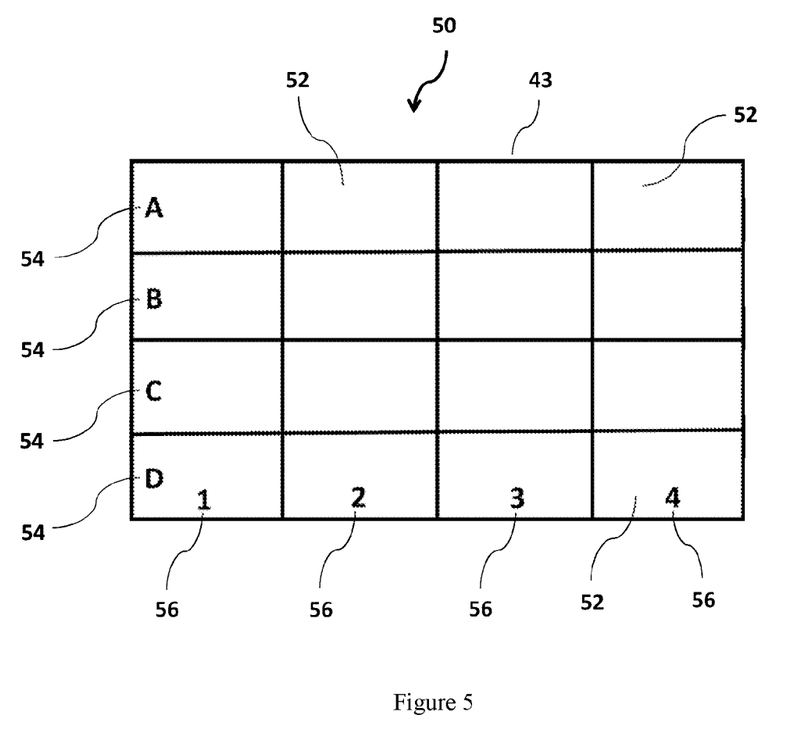
FIG. 5 shows a schematic view of a representation on a display of a portion of a wall forming part of an outer surface of a furnace.

FIG. 5 shows a schematic side view of a representation on a display of a portion of a wall 50, which is part of outer surface 43 of a furnace. Wall 50 comprises a plurality of bricks 52 made of refractory material. A grid consisting of a first set of mapping labels 54, vertically oriented, and a second set of mapping labels 56, horizontally oriented, may be externally placed on outer surface 43, to facilitate the tracking of the specific regions of the furnace being monitored in real time or over a certain period of time. Preferably, outer surface 43 is labeled with letters or numbers in rows and columns using labels 54, 56. Labels 54, 56 should be capable of withstanding the relatively high temperatures, which may reach over 1000° F., on outer surface 43.

In reference to FIGS. 1 to 5, preferably, customized software is installed in control unit 12 to enable the mapping of outer surface 43 of furnace 30, based on mapping labels 54, 56. The dimensions and layout of furnace 30, including each of layers 36, 38, 40, and 42, type of material, and layer thickness are setup in the customized software installed in control unit 12. In addition, the rows and columns as mapped on outer surface 43 of furnace 30, according to labels 54, 56, are correspondingly mapped onto a software layout of furnace 30 and installed in control unit 12 to enable proper mapping and tracking of each inspection of a region of furnace 30.

Figure 6:
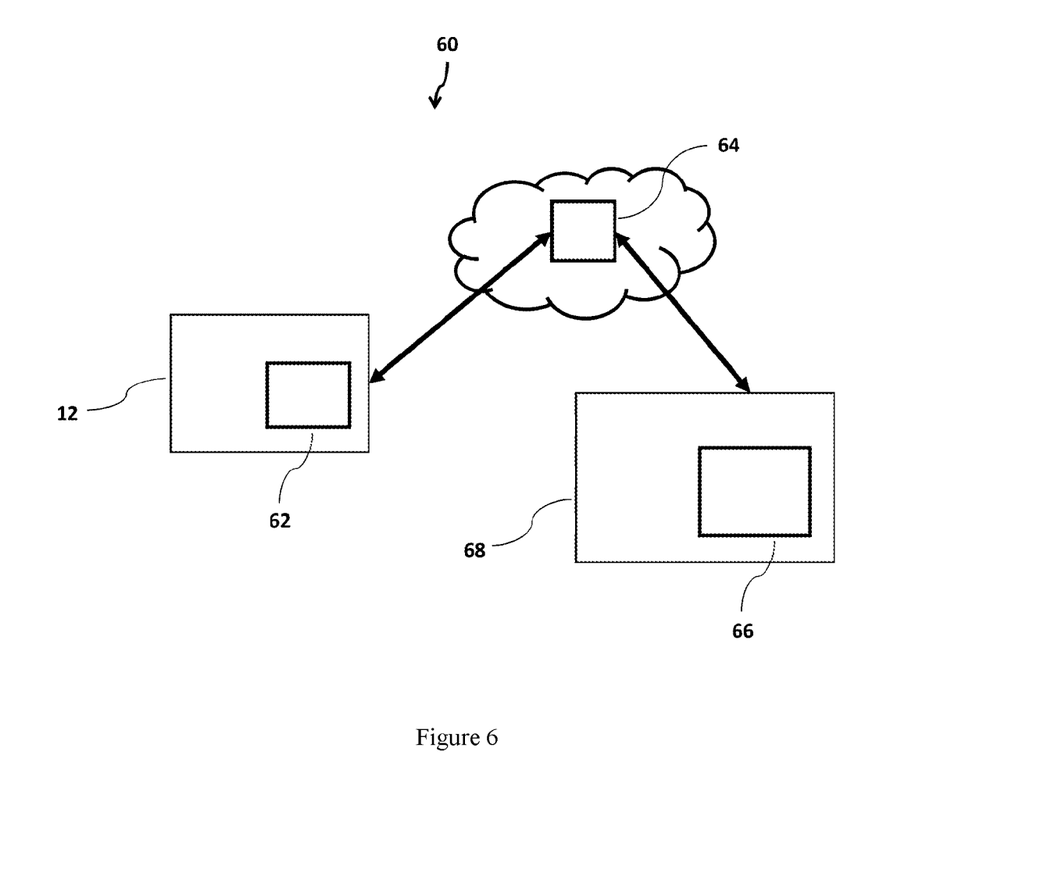
FIG. 6 shows a configuration of a management software architecture in accordance with certain aspects of a configuration.

In accordance with certain aspects of a configuration of the invention, an asset life optimization system comprises a monitoring system integrated with a management software subsystem. More specifically, in a preferred configuration, each of the above-described configurations, in reference to FIGS. 1 to 4, may be integrated with a management software subsystem to implement an asset life optimization system, wherein furnace 30 represents such asset. Thus, the management software subsystem may be used to perform and control the monitoring, recording, mapping, visualization, diagnosing, analysis, and tracking of the status of furnace 30. In particular, FIG. 6 shows a configuration of a management software subsystem architecture 60, comprising a first software module 62 installed in control unit 12, a cloud computer subsystem 64, and a second software module 66 installed in a client computer 68. Management software subsystem architecture 60 enables the data collection and storage by control unit 12, the data transfer and processing, and the inspection reports generation.

In reference to FIGS. 1 to 6, preferably, before inspecting an area of furnace 30, a map of the design of furnace 30 is downloaded to control unit 12. Then, a user may operate software module 62 to enter on control unit 12 the specific region of furnace 30 to be inspected. This may be done by selecting on control unit 12 the corresponding block or section, according to the identification of rows and columns on outer surface 43 of furnace 30, in reference to mapping labels 54, 56.

More preferably, software module 62 enables one or more navigation buttons on control unit 12 to allow a user to select a region of furnace 30 to be inspected, or to control a function, such as triggering the collection of data, of sensor head 14 or device 14a. During inspection, software module 62 stores on control unit 12 all the data collected for each inspected section of outer surface 43 of furnace 30.

Most preferably, the map of the design of furnace 30 is uploaded to cloud computer subsystem 64, and second software module 66 allows downloading this map from cloud computer subsystem 64 to control unit 12. Alternatively, software module 62 may be enabled to download this map directly from cloud computer subsystem 64.

Once the inspection is completed, software module 62 may be used to transfer the data, corresponding to the inspected block or section of furnace 30, from control unit 12 to cloud computer subsystem 64. Then, second software module 66 may be used to download the data from cloud computer subsystem 64 into client computer 68. Alternatively, a user may operate second software module 66 to enable the transfer of data from control unit 12 to cloud computer subsystem 64. In any case, second software module 66 may be used for evaluation and analysis of the data stored in either cloud computer subsystem 64 or client computer 68. This data analysis may include the use of data processing and image processing algorithms and signal processing visualization techniques.

After the collected data have been processed, software module 66 may generate inspection reports to organize inspection data, visualize potential molten material penetration, and provide analytics on furnace degradation to optimize the maintenance plan of furnace 30. Typically, an inspection report may include a two-dimensional or a three-dimensional visualization providing information of the outer walls of furnace 30. For example, a report may indicate the thickness of the refractory material, with mapping labels 54, 56 or color-coded representation, corresponding to regions where the thickness may have reached certain levels, according to a predefined criteria.

More specifically, an inspection report may include a two-dimensional visualization of outer surface 43 of furnace 30, similar to the representation shown in FIG. 5, displaying color-coded or warning information, corresponding to a flaw or the thickness of the refractory material and according to predetermined thickness levels (e.g., normal, moderate, or critical) for each area of outer surface 43 that have been inspected. Likewise, an inspection report may include a three-dimensional visualization of a cross-sectional view of wall 50 showing the status of each of layers 36, 38, 40, and 42 of furnace 30.

In addition, inspection reports may provide information in terms of a thickness profile over time for a specific block or section of furnace 30 to observe the trend of the material degradation and estimate appropriate times for repairs or furnace utilization. Other inspection reports may include the level of penetration of molten material 34 into each of layers 36, 38, 40, and 42 of furnace 30 and temperature corresponding to a specific block or section of furnace 30 to identify areas of potential breakage and prevent damage to furnace 30 and the surrounding equipment and personnel. Software module 66 is able to keep record of each inspection, compute refractory material erosion rate, provide a history of the degradation of each of layers 36, 38, 40, and 42 of furnace 30, determine the impact of the melting process, and evaluate the performance of each of layers 36, 38, 40, and 42 of furnace 30 for specific types of molten material used.

In another configuration, and in reference to FIGS. 2 and 6, client computer 68 may be directly connected to control unit 12. In other words, client computer 68 in FIG. 6 may be used as computer-based processor 20 in FIG. 2. In this case, all data collection, storing, transferring, processing, and reporting may be performed locally.

Those skilled in the art will realize that client computer 68 may be connected to or integrated with an external computer or server having a secure database and a backup storage system. This external computer or server may replace cloud computer subsystem 64. Preferably this external computer or server comprises a web application such that a user can remotely access and visualize the results of a furnace inspection through a web or smartphone platform. Likewise, those skilled in the art will recognize that data processing and image processing algorithms may be implemented by using one or a combination of more than one technique. These techniques may include Fourier transform, spectral analysis, frequency- and time-domain response analyses, digital filtering, convolution and correlation, decimation and interpolation, adaptive signal processing, waveform analysis, and data windows and phase unwrapping for data processing; and time domain, back projection, delay and sum, synthetic aperture radar imaging, back propagation, inverse scattering, and super-resolution, either with or without the application of differential imaging, for image processing.

The various embodiments have been described herein in an illustrative manner, and it is to be understood that the terminology used is intended to be in the nature of words of description rather than of limitation. Any embodiment herein disclosed may include one or more aspects of the other embodiments. The exemplary embodiments were described to explain some of the principles of the present invention so that others skilled in the art may practice the invention. Obviously, many modifications and variations of the invention are possible in light of the above teachings. The present invention may be practiced otherwise than as specifically described within the scope of the appended claims and their legal equivalents.

The various embodiments have been described herein in an illustrative manner, and it is to be understood that the terminology used is intended to be in the nature of words of description rather than of limitation. Any embodiment herein disclosed may include one or more aspects of the other embodiments. The exemplary embodiments were described to explain some of the principles of the present invention so that others skilled in the art may practice the invention. Obviously, many modifications and variations of the invention are possible in light of the above teachings. The present invention may be practiced otherwise than as specifically described within the scope of the appended claims and their legal equivalents.

We claim:

1. A system for evaluating a status of a material, comprising:

a. a sensor head comprising an antenna, a software-controlled device, a radiofrequency module, wherein said antenna is configured to enable a transmission of a first radiofrequency signal from said radiofrequency module onto an area of said material to be evaluated, and to enable a reception by said radiofrequency module of a second radiofrequency signal received from said area of said material to be evaluated, and wherein said software-controlled device comprises first executable computer code configured to operate said radiofrequency module and collect a set of data from said radiofrequency signal received by said radiofrequency module;

b. a control unit comprising a computer-based processor having a second executable computer code and a data storage unit, wherein said second executable computer code is configured to control an operation of said sensor head and to manage a communication between said sensor head and said control unit, and wherein said set of data may be stored in said data storage unit;

c. a communication channel that enables said communication between said sensor head and said control unit; and d. a software management subsystem comprising a first software module executable by said computer-based processor and configured to allow a user to operate said control unit and to perform and control a function for handling said set of data for evaluating said status of said material.

2. The system of claim 1, wherein said software management subsystem is further configured to process said set of data to estimate a remaining period of useful operation of an asset comprising said material.

3. The system of claim 2, wherein said asset is a furnace.

4. The system of claim 2, wherein said asset further comprises an internal material of a different type from said material to be evaluated and wherein said internal material is adjacent to at least one layer of said material to be evaluated.

5. The system of claim 4, wherein said status of said material to be evaluated is a level of penetration of said internal material into said at least one layer of said material to be evaluated.

6. The system of claim 1, wherein said status of said material is a thickness of said material.

7. The system of claim 1, wherein said status of said material is a flaw of said material.

8. The system of claim 1, wherein said communication channel further comprises a set of cables, including at least one line selected from the group consisting of a communication line, a control line, and a power line.

9. The system of claim 8, wherein said set of cables further comprises at least one element selected from the group consisting of a triggering switch and a navigation control.

10. The system of claim 1, further comprising a client computer integrated with said software management subsystem, wherein said software management subsystem comprises a second software module, which may be executable by said client computer and is configured to allow a user to operate said client computer and to perform and control a function for processing said set of data for evaluating said status of said material.

11. The system of claim 10, wherein said client computer controls said control unit.

12. The system of claim 10, wherein said client computer communicates with said control unit through an element comprising at least one of a wireless channel, a physical connection, and an external computer.

13. The system of claim 1, wherein said software management subsystem is configured to generate an inspection report about said status of said material based upon a time of travel of at least one of said first radiofrequency signal and a second radiofrequency signal.

14. The system of claim 13, wherein said inspection report includes a visualization of said status of said material selected from the group consisting of a two-dimensional visualization and a three-dimensional visualization.

15. The system of claim 14, wherein said visualization includes color-coded information corresponding to a predetermined level of said status of said material.

16. The system of claim 13, wherein said time of travel of said at least one of said first radiofrequency signal and said second radiofrequency signal is different from a time of travel of a spurious signal, including a reflection of at least one of said first radiofrequency signal and said second radiofrequency signal from a portion of said antenna, by an extent so as to enable temporal isolation of said at least one of said first radiofrequency signal and said second radiofrequency signal from said spurious signal.

17. The system of claim 1, wherein determining said status of said material from said set of data is performed by said second computer executable code based upon a known propagation velocity of at least one of said first radiofrequency signal and said second radiofrequency signal travelling through said material.

18. The system of claim 1, wherein said second radiofrequency signal, received from said area of said material to be evaluated, results from a reflection of said first radiofrequency signal, transmitted by said radiofrequency module.

19. The system of claim 1, wherein said function for handling said set of data includes at least one of measuring, storing, monitoring, recording, processing, mapping, visualizing, transferring, analyzing, tracking, and reporting of at least a portion of said set of data for evaluating said status of said material.

20. The system of claim 1, wherein said control unit is part of a portable device.

21. The system of claim 20, wherein said portable device is a handheld electronic device having the capability to store and display data to the user.

22. The system of claim 1, wherein said sensor head is physically integrated into a single unit.

23. The system of claim 1, further comprising a mechanical attachment having a first end coupled to said antenna and a second end coupled to said at least one element, wherein said mechanical attachment enables an extension of a distance between said antenna and said at least one element.

24. The system of claim 23, wherein said first end of said mechanical attachment comprises a quick-connect system to enable said antenna to easily couple to said first end of said mechanical attachment.

25. The system of claim 23, wherein said mechanical attachment comprises at least one of a gooseneck unit, a collapsible part, a flexible piece, a telescopic pole, a foldable component, an angled-section arm, and a building block to enable said antenna to reach out an area of said material having difficult access.

26. The system of claim 1, wherein said antenna has an end conformal to a surface of said material to be evaluated.

* * * * *